United States Patent [19]

Schaper et al.

[11] Patent Number: 4,719,041

[45] Date of Patent: Jan. 12, 1988

[54] 1-ALKYL/ALKENYL CYCLOHEXAN-1-OLS AS PERFUMES

[75] Inventors: Ulf-Armin Schaper, Krefeld; Siegfried Bloesl, Schwaebisch-Gmuend; Klaus Bruns, Krefeld-Traar; Benno Streschnak, Krefeld, all of Fed. Rep. of Germany

[73] Assignee: Henkel Kommanditgesellschaft auf Aktien, Duesseldorf, Fed. Rep. of Germany

[21] Appl. No.: 28,288

[22] Filed: Mar. 20, 1987

[30] Foreign Application Priority Data

Mar. 21, 1986 [DE] Fed. Rep. of Germany ....... 3609525

[51] Int. Cl.⁴ .......................... A61K 7/46; C07C 35/08

[52] U.S. Cl. ................................ 252/174.11; 568/835; 568/834; 568/832; 512/23

[58] Field of Search .................... 252/522 R; 568/835, 568/834, 832

[56] References Cited

U.S. PATENT DOCUMENTS 4,113,645 9/1978 DeSimone .......................... 252/187

OTHER PUBLICATIONS

Giguere et al., "Chemical Abstracts" vol. 97 (1982), 19834a.

Hoffman et al., "Chemical Abstracts" vol. 98 (1983), 160952p.

Hoffmann et al., "Chemical Abstracts" vol. 102 (1985), 185290k.

Hoffmann et al., "Chemical Abstracts" vol. 105 (1986), 24466u.

Chemical Abstracts, 87:169574x.

Chemical Abstracts, 87:137622h.

J. S. Jellinek: "Parfumieren von Produkten", Dr. Alfred Huthig Verlag, Heidelberg, 1976, pp. 100–101.

Wallach in Liebigs Ann. Chem. 360, 54.

Barbier in Helv. Chim. Acta 23, 519, 1940.

*Primary Examiner*—Werren B. Lone

*Attorney, Agent, or Firm*—Ernest G. Szoke; Henry E. Millson, Jr.; Mark A. Greenfield

[57] ABSTRACT

The invention relates to the use as perfumes of 1-alkyl-/alkenyl cyclohexan-1-ols corresponding to the general formula

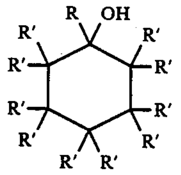

in which R is a $C_{1-4}$ alkyl or a $C_{2-4}$ alkenyl, 0 to 3 of the 10 substituents R′ are methyl and the balance of the 10 substituents R′ are hydrogen, in compositions containing active chlorine, and perfumed compositions so obtained.

11 Claims, No Drawings

1-ALKYL/ALKENYL CYCLOHEXAN-1-OLS AS PERFUMES

BACKGROUND OF THE INVENTION

1. Field of the Invention

This invention relates to the use of certain 1-alkyl-/alkenyl cyclohexan-1-ols as perfumes in compositions containing active chlorine.

2. Statement of Related Art

In many consumer goods, for example in body-care preparations or fabric softeners, problems regarding the stability of the perfumes used are unknown. By contrast, compositions containing active chlorine, such as dishwashing detergents and/or scouring preparations and the like, destroy most perfumes so that perfuming with the desired fragrance notes is no longer possible (cf. J. S. Jellinek: "Parfumieren von Produkten", pp. 100–101, Dr. Alfred Huthig Verlag (pub.) Heidelberg, 1976). In addition, destruction of the perfumes is often accompanied by an undesirably high reduction of the active chlorine content.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides methods for using certain perfumes which are stable in compositions containing active chlorine, methods for preparing such compositions, and the compositions themselves.

It has surprisingly been found that no problems of stability arise where the inventive perfumes which are one or more 1-alkyl/alkenyl cyclohexan-1-ols corresponding to the general formula

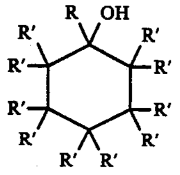

in which R is a $C_{1-4}$ alkyl or a $C_{2-4}$ alkenyl, 0 to 3 of the 10 substituents R′ are methyl and the balance of the 10 substituents R′ are hydrogen, are employed in compositions containing active chlorine, or capable of generating active chlorine upon standing, exposure to moisture or heat, etc.

The preferred species within the above formula are (1-ethyl) and (1,3,3,5-tetramethyl) cyclohexan-1-ol, both of which are included in the examples which follow.

1-ethyl cyclohexan-1-ol [Wallach in Liebigs Ann. Chem. 360, 50] and 1,3,3,5-tetramethyl cyclohexan-1-ol [Barbier in Helv. Chim. Acta 23, 519 (1940)] are compounds known from the literature and are obtained by reaction of the ketones with the corresponding Grignard compounds. The odor of 1,3,3,5-tetramethyl cyclohexan-1-ol is described only as camphory. However, there is no information in either of these two literature references on the stability of the alcohols in mixtures containing active chlorine.

The odor of the chlorine-stable cyclohexan-1-ols may be characterized as camphory, earthy, woody.

The cyclohexan-1-ols which are used in accordance with the invention in compositions containing active chlorine were subjected to a storage test. It was surprisingly found that, even after one year at room temperature, no changes in odor occurred either in liquid or in solid compositions containing active chlorine.

EXAMPLES

General procedure for the preparation of 1-alkyl/alkenyl cyclohexan-1-ols

In a thoroughly heated apparatus, 20 ml of a solution of 0.5 mol alkylhalide in 150 ml ether were added dropwise to 0.5 mol magnesium chips in 50 ml anhydrous ether. When the Grignard reagent began to form, the rest of the alkylhalide solution was added quickly enough so that the ether boiled gently. After the addition, the mixture was heated under reflux for about another 30 minutes.

0.45 mol of the corresponding cyclohexanone in 100 ml ether was added dropwise to the cooled Grignard solution, followed by stirring under reflux for about 30 minutes.

For working up, the reaction mixture was cooled to 0° C. and poured carefully into a cold, saturated $NH_4Cl$-solution (approx. 300 ml). The ether phase was then separated off and the aqueous phase extracted twice with 80 ml ether. The combined etheral phases were washed with saturated sodium hydrogen carbonate and sodium chloride solution. After drying with sodium sulfate and evaporation of the solvent, the residue was distilled in vacuo.

The following compounds were prepared by this method:

(A) 1-ethyl cyclohexan-1-ol
odor: camphory, woody.

(B) 1,3,3,5-tetramethyl cyclohexan-1-ol
odor: earthy.

Typical bouquet for liquid and solid compositions containing active chlorine such as used in storage tests 100 parts by weight 1-cyanododecane
150 parts by weight 2,6-dimethylheptan-2-ol
100 parts by weight 1-ethyl cyclohexan-1-ol [PERFUME]
100 parts by weight dihydromyrcenol
150 parts by weight tetrahydrolinolool
100 parts by weight terpineol
300 parts by weight dipropylene glycol The above bouquet, or one prepared with similar ingredients well known in the art, may be employed in any conventional or new composition which contains active chlorine, or is capable of releasing active chlorine upon storage and/or exposure to moisture. The formulations of such compositions do not affect the perfumes of this invention except as disclosed herein, and therefore do not form a part of this invention. The compositions may comprise any dishwashing, laundry, commercial or household detergent and/or scouring preparation, to which the perfumes of this invention are added. The amount of addition will vary with the composition ingredients, amount of free chlorine, etc. but must be in at least a perfume-effective amount. The addition may be in any order of ingredients, and may be of the perfume per se or of a conventional bouquet of the type abovementioned. There are no limitations as to physical conditions of the addition or the compositions, other than those already known in the art. The compositions with the added perfumes are considered novel.

We claim:

1. A method for perfuming a composition containing active chlorine, or capable of generating active chlorine, comprising incorporating within said composition at least a perfume-effective amount of at least one compound of the formula:

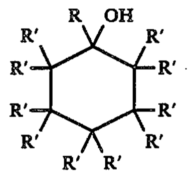

wherein:

R is a $C_{1-4}$ alkyl or $C_{2-4}$ alkenyl;

0 to 3 of the 10 substituents R' are methyl; and the balance of the 10 substituents R' are hydrogen.

2. The method of claim 1 wherein R is ethyl and all R' substituents are hydrogen.

3. The method of claim 1 wherein said compound is 1,3,3,5-tetramethyl cyclohexan-1-ol.

4. The method of claim 1 wherein said composition is a detergent and/or scouring preparation.

5. A perfumed composition obtained by the method of claim 1.

6. A perfumed composition obtained by the method of claim 2.

7. A perfumed composition obtained by the method of claim 3.

8. A perfumed composition obtained by the method of claim 4.

9. In a detergent and/or scouring composition containing active chlorine and/or which is capable of generating active chlorine, the improvement wherein a perfume-effective amount of at least one compound is added, said compound being of the formula:

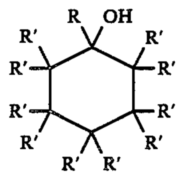

wherein:

R is a $C_{1-4}$ alkyl or $C_{2-4}$ alkenyl;

0 to 3 of the 10 substituents R' are methyl; and the balance of the 10 substituents R' are hydrogen.

10. The composition of claim 9 wherein R is ethyl and all R' substituents are hydrogen.

11. The composition of claim 9 wherein said compound is 1,3,3,5-tetramethyl cyclohexan-1-ol.

* * * * *